United States Patent [19]
Khaled

[11] Patent Number: 5,977,073
[45] Date of Patent: Nov. 2, 1999

[54] NUTRIENT COMPOSITION FOR TREATMENT OF IMMUNE DISORDERS

[75] Inventor: F. Mahnaz Khaled, Pelham, Ala.

[73] Assignee: Life Sciences' Technologies, Inc., Birmingham, Ala.

[21] Appl. No.: 07/711,530

[22] Filed: Jun. 6, 1991

[51] Int. Cl.$^6$ .................................................. A61K 38/00
[52] U.S. Cl. ......................... 514/19; 530/331; 546/301; 549/315; 549/408; 585/351; 562/553
[58] Field of Search ............................. 530/331; 514/19; 546/301; 549/408, 315; 585/351; 562/553

[56] References Cited

U.S. PATENT DOCUMENTS

| | | | |
|---|---|---|---|
| 4,466,978 | 8/1984 | Naylor | 424/280 |
| 4,710,489 | 12/1987 | Meister | 530/331 |
| 4,761,399 | 8/1988 | Pilotto et al. | 514/19 |
| 4,871,528 | 10/1989 | Tognella et al. | 424/10 |
| 4,927,808 | 5/1990 | Kitahara et al. | 514/19 |
| 4,968,671 | 11/1990 | Asano et al. | 514/18 |
| 5,102,871 | 4/1992 | Furukawa et al. | 530/331 |

OTHER PUBLICATIONS

Mason et al, J. of Acquired Immune Deficiency Syndromes 2: 235–247, 1989.
Roederer et al., Proc. Natl. Acad. Sce. USA 87: 4884–4888, 1990.
Herzlich et al., American Journal of Hematology 33:177–183, 1990.
Weislow et al., Articles 81:577, 1989.
Salonen et al., Am. J. Clin. Nutr. 48:1226, 1988.
Blum et al., Alcohol. 5:481, 1989.
Dommissee, Am. J. Psychiatry 148(2):279, 1991.

*Primary Examiner*—Cecilia J. Tsang
*Attorney, Agent, or Firm*—Lyon & Lyon LLP

[57] ABSTRACT

A composition and method for its use in treatment of an immune disorder in a mammal. The composition includes, in relative amounts, between 50 and 3000 mg of a purified compound selected from oxidized and unoxidized gamma-L-glutamyl-L-cysteinylglycine, gamma-L-glutamyl-L-cysteine, N-acetyl-L-cysteine, N-acetyl-L-cysteine-glycine, and any other pharmaceutically active compound which directly enhances the level of gamma-L-glutamyl-L-cysteinylglycine in a mammal, and any salt or ester of said compound, between 50 and 3000 mg purified L-glutamine, between 50 and 10,000 mg purified vitamin C, between 50 and 500 mg purified vitamin E, between 10 and 100 mg purified Beta-carotene, and between 1 and 25 mg purified vitamin $B_6$.

24 Claims, 1 Drawing Sheet

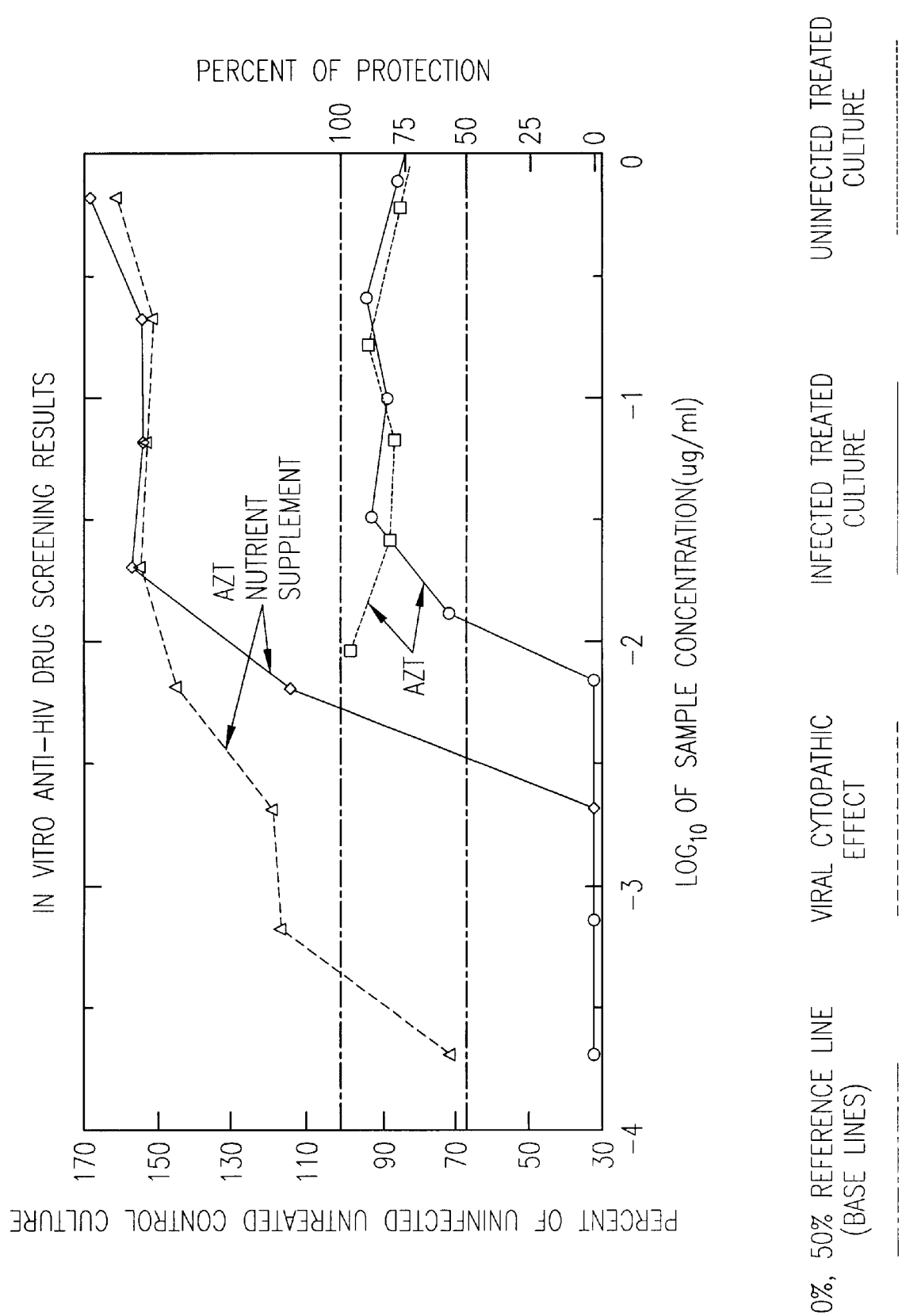

NUTRIENT COMPOSITION FOR TREATMENT OF IMMUNE DISORDERS

BACKGROUND OF THE INVENTION

This invention relates to nutritional supplements.

The human diet is the subject of many standard texts. Such a diet may include use of dietary supplements, e.g., in the form of pills or liquids, which may include one or more vitamins, minerals, and essential or non-essential amino acids. In addition, it is common for people to alter their diet to change their input of fats or lipids, proteins, and carbohydrates.

It is recognized that the diet of a person may have some affect on their health. For example, Corman, 69 *Med. Clin. North Am.*, 759, 1985 describes the influence of specific nutrients on specific immune mechanisms; Huang et al., 34 *Clin. Chem.* 1957, 1987 describe malnutrition in persons infected with the virus HIV, manifested by deficiency in several essential nutrients; Herzlich et al, 33 *Am. J. Hematol* 177, 1990 describe the effect of treatment of Acquired Immunodeficiency Syndrome (AIDS, caused by HIV infection) with 3'-azido-3' deo-xythiamidine (AZT), including the depletion of folic acid and vitamin $B_{12}$, and is unclear "whether the benefit [of folate or vitamin $B_{12}$ supplementation] exceeds the risks . . . ;" Moseson et al., 2 *J. Acquired Immune Deficiency Symptoms*, 235, 1989 state that "recommendations for dietary supplementation in HIV-infected individuals are premature and possibly hazardous;"0 and Roederer et al., 87 *Proc. Natl. Acad. Sci. USA*, 4884, 1990, suggest N-acetyl-L-cysteine as "a possible therapeutic agent in AIDS."

Glutathione and related compounds are suggested as therapeutic agents by Tognella et al., U.S. Pat. No. 4,871,528, (to treat tumors); Pilotto et al., U.S. Pat. No. 4,761,399 (to treat pathologic syndromes); Kitahara et al., U.S. Pat. No. 4,927,808 (to treat necrosis and a multitude of related diseases); Asano et al., U.S. Pat. No. 4,968,671 (to treat ischemic heart disease); and Naylor, U.S. Pat. No. 4,466,978 (to lower bodyweight). Reduced glutathione is a free radical scavenger in cells which is usually recycled in vivo from oxidized glutathione with the help of nutrients such as vitamins C, and E, beta-carotene, selenium, and chromium. Some dipeptides, including N-acetyl cysteine are capable of increasing glutathione levels in the plasma (Pilotto et al., supra and Kitahara et al., supra).

SUMMARY OF THE INVENTION

Applicant has discovered that a nutrient composition can be used as an adjunct to therapeutic drugs in treatment of diseases affecting the immune system, as well as in other diseases or injured states. Without being bound to any theory, applicant believes that provision of the nutrients within this nutrient composition aids in increasing the amount of replication of the causative organism of the disease, and thus enhances the effect of drugs which exert maximum effectiveness on growing organisms. In addition, such nutrients increase the health of a patient to which they are administered. Thus, the nutrient composition and any standard drug treatment act synergistically to increase the quality of life, and life expectancy of a patient.

Applicant has recognized that the body's immune system can be compromised because of poor dietary habits or starvation, various environmental stresses that include physical, psychological, infection, trauma, ischemia, radiation, chemical exposure, cigarette, alcohol or narcotic substance abuse, and the toxic effect of one or more therapeutic drugs. A paradigm of such stress is found in AIDS, which appears to involve several nutritional aberrations. HIV is a T-cell lymphotropic retrovirus that severely infects T-helper cells, and causes severe malnutrition. Such malnutrition increases the susceptibility of the patient to opportunistic diseases that form the basis of AIDS or AIDS related complex (ARC). Among the deficient nutrients in AIDS patients, or in HIV-infected patients, are anti-oxidants such as vitamins A, C, and E, and glutathione (gamma-L-glutamyl-L-cysteinylglycine.

Applicant proposes that the above-described immune disorders which are caused by a virus and/or bacterium can be treated by using antiviral and/or antibacterial pharmacological agents (generically called antiorganism agents), together with a nutritional supplement which both bolsters the immune competence of the patient, and reduces the toxicity of the antiorganism agent. The nutritional supplement accelerates replication of the causative virus or bacterium, and creates an ideal condition for the antiorganism agent to exert its maximum effectiveness in killing or injuring the organism. A specific composition of this mixture of nutrients is provided in Table 1 where the appropriate relative ranges of each nutrient in the mixture is noted. These ranges reflect the variation in individual patient requirements. Such requirements will depend on body weight, age, sex, and the type of disease to be treated. In general, this range is ideal for provision within a capsule, pill, or liquid tonic for oral administration to a 70 kg human.

TABLE 1

Individual Nutrient and the Ranges in Necessary Quantity of each Nutrient

| Nutrients | Ranges of Amount |
| --- | --- |
| L-Arginine | 50–5,000 mg |
| Beta-Carotene | 10–100 mg |
| Chromium | 5.0–50 µg |
| Folic Acid | 50–150 µg |
| L-Glutamine | 50–3,000 mg |
| Glutathione | 50–3,000 mg |
| Iron | 1.0–50 mg |
| Magnesium | 10–50 mg |
| Pantothenic Acid | 5–50 mg |
| Riboflavin | 1.0–25 mg |
| Selenium | 10–1,000 µg |
| Thiamine | 5–50 mg |
| Vitamin A | 0.5–10 mg |
| Vitamin $B_6$ | 1.0–25 mg |
| Vitamin $B_{12}$ | 0.5–50 µg |
| Vitamin C | 50–10,000 mg |
| Vitamin E | 50–500 mg |
| Zinc | 1.0–50 mg |

The nutrients described in Table 1 can be used in the form of physiologically acceptable salts and esters thereof. The glutathionine may be in its oxidized or reduced form or may be replaced with any of its immediate biochemical precursors, such as gamma-L-glutamyl-L-cysteine, N-acetyl-L-cysteine, and N-acetyl-L-cysteine-glycine, and their salts or esters, or any other pharmaceutically active compound that directly enhances the level of glutathione in the patient. Examples of such compounds are well known to those in the art, and are found, inter alia, in Pilotto et al., supra. By "directly enhances" is meant that the compound is converted into glutathione by only one or two biochemical reaction steps; the phrase does not include compounds, such as glucose, which eventually may be converted to glutathione.

Thus, in a first aspect the invention features a composition adapted for treatment of an immune disorder in a mammal.

This composition comprises, consists, or consists essentially of the amounts shown in Table 1 of a purified compound selected from oxidized and unoxidized gamma-L-glutamyl-L-cysteinylglycine, gamma-L-glutamyl-L-cysteine, N-acetyl-L-cysteine, N-acetyl-L-cysteine-glycine, and any other pharmaceutically active compound which directly enhances the level of gamma-L-glutamyl-L-cysteinylglycine in a mammal, and any salt or ester of said compound, purified L-glutamine, purified vitamin C, purified vitamin E, purified Beta-carotene and purified vitamin $B_6$. Generally, such a composition is provided within any pharmaceutically-acceptable buffer.

In preferred embodiments the composition is provided with one or more (preferably all) of the following purified components in an amount shown in Table 1: L-arginine, chromium, folic acid, iron, magnesium, selenium, pantothenic acid, riboflavin, thiamine, vitamin A, vitamin $B_{12}$, and zinc.

By "purified" is meant that the compound or specific component is provided in a form acceptable by the United States Food and Drug Administration for administration to an animal or human patient. The term is meant to exclude provision of the specific component as part of an animal or plant which may be eaten by the mammal to be treated. In general such compounds and components will be provided in a very pure form commonly used in formulating existing vitamin pills and the like.

In a related aspect, the invention features a method for a treatment of immune disorders such as Acquired Immuno-deficiency Syndrome, Herpes Infection, Hepatitis, or the disorder caused by traumatic injury, cancer, or diabetes, by administration of a composition as described above. The composition is provided in an amount sufficient to alleviate one or more symptoms of the immune disorder.

By "symptom" is meant the outward signs, as well as any measurable indicia, of a disease state commonly recognized as indicative of the disease to be treated by medical doctors or veterinarians of ordinary skill in the art.

In a related aspect, the invention features a method for treatment of an immune disorder in a mammal. A mammal having such a disorder caused by a virus or bacterium is identified, and the mammal then provided with an antiviral or antibacterial agent with some toxicity to the mammal (i.e., having some affect on the nutritional state of the mammal), and a nutritional composition (as described above) in an amount sufficient to reduce the toxicity of the agent and accelerate replication of the virus or bacterium.

In addition, the invention includes a similar method for treatment of cardiovascular disease, mental disease, drug addition, and hair loss in a mammal, with the composition being provided in an amount sufficient to alleviate one or more symptoms of such diseases or conditions.

Examples of cancers which may be treated include Karposi's Sarcoma, lymphoma, and non-Hodgkin lymphoma; the disease is preferably treated simultaneously with some drug therapy, such as AZT, in an amount sufficient to alleviate a symptom of the disease; the causative organism of the infection is HIV, herpes virus, hepatitis virus, or a virus or bacterium causative of a respiratory disorder; the injury is a traumatic injury resulting from fractures, laceration or burns; the disease may be high blood pressure, hypertension, obesity or ischemic heart disease; in addition, the disease may be tardive dyskinesia, and hyperactivity in children; and the addiction may be addiction to psychoactive drugs, narcotic drugs, nicotine or alcohol.

The above nutritional composition, and methods for use of that composition, have been found to significantly enhance the efficacy of treatment of diseases in conjunction with one or more routine drug therapies. The effect is profound and unexpected, in that many symptoms of severe diseases can be significantly alleviated.

Other features and advantages of the invention will be apparent from the following description of the preferred embodiments thereof, and from the claims.

DESCRIPTION OF THE PREFERRED EMBODIMENTS

The drawing will first briefly be described.

Drawing

The drawing is a graphical representation of results of experiments comparing the use of AZT alone, and AZT with a nutrient composition of the invention.

Nutrient composition

The nutrient composition is generally described above. Those of ordinary skill in the art will recognize that the most important components of this nutrient composition include glutathione, or its equivalent, in combination with glutamine, vitamins E and C, and Beta-carotene. However, it is preferred that all of the components listed in Table 1 be included for full treatment of the various diseased discussed below.

An example of the use of the nutrient composition described in Table 1 for treatment of cells infected with HIV, or humans infected with HIV is provided below. Those of ordinary skill in the art will recognize that this example is not limiting in the invention, and that such a nutrient composition can be readily used in treatment of the other diseases discussed above. The nutrient composition is formulated by use of standard procedures and may be administered by any of a number of standard procedures, including oral administration, intramuscular, or intravenous injection.

Table 2 shows the precise chemical composition of the nutrient composition used in the examples below.

TABLE 2

| Nutrients | Amount per capsule |
|---|---|
| L-Arginine | 75 mg |
| Beta-Carotene | 15 mg |
| Chromium | 15 µg |
| Folic Acid | 100 µg |
| L-Glutamine | 150 mg |
| Glutathione | 250 mg |
| Iron | 10 mg |
| Magnesium | 20 mg |
| Pantothenic Acid | 25 mg |
| Riboflavin | 10 mg |
| Selenium | 25 µg |
| Thiamine | 10 mg |
| Vitamin A | 4 mg |
| Vitamin $B_6$ | 8 mg |
| Vitamin $B_{12}$ | 1.0 µg |
| Vitamin C | 500 mg |
| Vitamin E | 150 mg |
| Zinc | 25 mg |

EXAMPLE 1

In Vitro Analysis

Following the procedures of Wieslow et al. 81 *Journal of National Cancer Institute* 577, 1989, (hereby incorporated by reference herein) $T_4$ lymphocytes (CEM cell line) were used in a soluble-formazan assay to assess the toxicity of the test material (AZT±nutritional supplement) and the recovery of T-cells from HIV infection.

In-Vitro Assay

Briefly, the test sample was dissolved in dimethyl sulfoxide and diluted 1:100 in RPMI cell culture medium to prepare serial half-log$_{10}$ dilutions. T$_4$ lymphocytes (CEM cell line) were added, and after about an hour HIV-1 added, resulting in a 1:200 final dilution of the test sample. Uninfected cells with the sample served as a control for the toxicity of the test sample. Infected and uninfected cells without the test sample served as the basic control. The cultures were then incubated at 37° C. in a 5% carbon dioxide atmosphere for six days. The tetrazohium salt was added to the wells and incubated until the formazon color was developed by the viable cells. Each well was analyzed spectrophotometrically to quantitate the formazan production, and also examined microscopically to detect viable cells. Test sample-treated virus-infected cells were compared to the test sample-treated noninfected cells, and with other appropriate controls on the same plate. The results are plotted graphically as described below.

Referring to the figure, the results are shown in graphical form for combination of AZT with the nutritional supplement described in Table 2, and for AZT alone.

FIG. 1 displays a plot of the log$_{10}$ of the concentrations of the test sample as μg/ml against the measured test values expressed as a percentage of the uninfected, untreated control values. The solid line connecting the rectangular symbols depicts the percentage of surviving HIV-infected cells treated with AZT, with or without the composition of Table 2, relative to uninfected, untreated controls and indicates the in vitro anti-HIV activity of the test samples. The broken line connecting the triangular symbols depicts the percentage of surviving uninfected cells treated with the test samples relative to the same uninfected, untreated controls, and expresses the in vitro growth inhibitory properties of the test samples. The viral cytopathic effect is given as the dotted reference line which indicates the extent of destruction of cells by the virus in the absence of treatment. The percent of protection calculated from the test results is presented on the right side of the graph. The therapeutic index (TI) of the test sample was estimated from the ratio of the values for 50% inhibitory concentration (IC$_{50}$) to the 50% values for the effective concentration (EC$_{50}$), i.e., TI=IC$_{50}$/EC$_{50}$.

The broken lines with triangular data points indicate the percent of uninfected T-cells. With AZT alone, about a 75% survival of T-cells was observed compared to control cells. With AZT and the nutritional supplemental such survival was increased to approximately 150%. Thus, the supplement enhances survival of T-cells in the presence of HIV.

The solid lines with rectangular data points indicate the therapeutic effectiveness of the material for the T-cells. With AZT alone, inhibition of growth of normal T-cells is observed, thus indicating toxicity. With a combination of AZT and the nutritional supplement, the growth is almost doubled. Thus, the nutritional supplement protects the cells from toxicity of AZT.

These data indicate that the therapeutic index of the drug nutrient combination therapy is almost ten times higher than that of AZT alone.

EXAMPLE 2

The above drug nutrient combination therapy was tested on three human subjects infected with HIV. Their clinical features are noted in Table 3.

TABLE 3

Clinical Features of Patients Receiving Immuno-Vite ™

| Patient No. & Diagnosis | Symptoms & Findings at Entry | Weeks on Nutritional Supplement | Clinical Observations |
|---|---|---|---|
| 1. AIDS-Post-PCP | Weight loss, Papulovesicular rash fever, malaise, T$_4$ = 1%, T$_8$ = 47% | 4 | Weight gained, no fever, and rash diminished Total lymphocyte count went up, although T$_4$ did not change, T$_8$ went up. |
| 2. ARC | Weight loss, malaise, Lymphadenopathy, yeast infection in gluteal area, rectal wart, T$_4$ = 320, T$_8$ = 1710 | 3 | Weight gained, increased energy, no raised lymph nodes, no yeast infections, diminished rectal wart, T$_4$ = 450, T$_8$ = 1220. |
| 3. ARC | Edemic, rash, fever, oral candidiasis, mouth sores (difficulty in talking), dementia | 2 | Improved skin lesions, mouth sores improved, (speak without difficulty), reduced confusion). |

AIDS (Acquired Immune Deficiency Syndrome)
PCP (Pneumocystis Carinii Pneumonia)
ARC (AIDS-Related Complex)

The patients were routinely taking AZT and other antiviral and antibacterial drugs. Clinical improvement of their condition was observed after only a short drug-nutrient combination therapy. Such significant improvements were observed within two weeks of initiation of the drug nutrient therapy.

Other embodiments are within the following claims.

I claim:

1. A composition adapted for use as an adjunct for treatment of an immune disorder in a mammal, wherein said immune disorder is selected from the group consisting of AIDS, ARC, cancer, and diabetes, and wherein said composition comprises components (a)–(f) as follows:

(a) between 50 and 3000 mg of a purified compound selected from oxidized and unoxidized gamma-L-glutamyl-L-cysteinylglycine, gamma-L-glutamyl-L-cysteine, N-acetyl-L-cysteine, and any other pharmaceutically active compound which directly enhances the level of gamma-L-glutamyl-L-cysteinylglycine in a mammal,
   (b) between 50 and 3000 mg purified L-glutamine,
   (c) between 50 and 10,000 mg purified vitamin C,
   (d) between 50 and 500 mg purified vitamin E,
   (e) between 10 and 100 mg purified Beta-carotene, and
   (f) between 1.0 and 25 mg purified vitamin B6.

2. The composition of claim 1, further comprising one or more of the following purified components:

between 50 and 5000 mg L-arginine,
   between 5 and 50 μg chromium,
   between 50 and 150 μg folic acid,
   between 1 and 5 mg iron,
   between 10 and 50 mg magnesium,
   between 5 and 50 mg pantothenic acid, between 1 and 2.5 mg riboflavin, between 5 and 50 mg thiamine, between 0.5 and 10 mg vitamin A, between 10 and 1000 µg selenium, between 0.5 and 5 µg vitamin $B_{12}$, and between 1 and 50 mg zinc.

3. The composition of claim 2, wherein said composition comprises each said component.

4. The composition of claim 1 or 3 wherein said compound is gamma-L-glutamyl-L-cysteinylglycine or an ester or salt thereof.

5. The composition of claim 1 or 3 wherein said compound is gamma-L-glutamyl-L-cysteine or an ester or salt thereof.

6. The composition of claim 1 or 3 wherein said compound is N-acetyl-L-cysteine or an ester or salt thereof.

7. A method for enhancing the effect of an agent which exerts an effectiveness on a mammal suffering from an immune disorder, wherein said immune disorder is selected from the group consisting of AIDS, ARC, cancer, and diabetes, comprising the step of administering to said mammal a composition comprising compounds (a)–(f) as follows:

(a) between 50 and 3000 mg purified compound selected from oxidized and unoxidized gamma-L-glutamyl-L-cysteinylglycine, gamma-L-glutamyl-L-cysteine, N-acetyl-L-cysteine, and any other pharmaceutically active compound which directly enhances the level of gamma-L-glutamyl-L-cysteinylglycine in a mammal, (b) between 50 and 300 mg purified L-glutamine, (c) between 50 and 10,000 mg purified vitamin C, (d) between 50 and 500 mg purified vitamin E, (e) between 10 and 100 mg purified Beta-carotene, and (f) between 1 and 25 mg purified vitamin $B_6$.

8. The method of claim 7, wherein said composition further comprises in one or more of the following purified components:

between 50 and 5000 mg L-arginine, between 5 and 50 mg chromium, between 50 and 150 mg folic acid between 1 and 5 mg iron, between 10 and 50 mg magnesium, between 5 and 50 mg pantothenic acid, between 1 and 2.5 mg riboflavin, between 5 and 50 mg thiamine, between 0.5 and 10 mg vitamin $B_{12}$, and between 1 and 50 mg zinc.

9. The method of claim 8, wherein said composition comprises each said component.

10. The method of claim 7, or 9 wherein said compound is N-acetyl-L-cysteine-glycine or an ester or salt thereof.

11. The method of claim 7, wherein said compound is gamma-L-glutamyl-L-cysteinylglycine or an ester or salt thereof.

12. The method of claim 7, wherein said compound is gamma-L-glutamyl-L-cysteine or an ester or salt thereof.

13. The method of claim 7, wherein said compound is N-acetyl-L-cysteine or an ester or salt thereof.

14. The method of claim 8 wherein said compound is gamma-L-glutamyl-L-cysteinylglycine or an ester or salt thereof.

15. The method of claim 8 wherein said compound is gamma-L-glutamyl-L-cysteine or an ester or salt thereof.

16. The method of claim 8 wherein said compound is N-acetyl-L-cysteine or an ester or salt thereof.

17. The composition of claim 1, wherein said immune disorder is selected from the group consisting of AIDS and ARC.

18. The method of claim 7, wherein said immune disorder is selected from the group consisting of AIDS and ARC.

19. A composition comprising components (a)–(f) as follows:

(a) between 50 and 3000 mg of a purified compound selected from oxidized and unoxidized gamma-L-glutamyl-L-cysteinylglycine, gamma-L-glutamyl-L-cysteine, N-acetyl-L-cysteine, and any other pharmaceutically active compound which directly enhances the level of gamma-L-glutamyl-L-cysteinylglycine in a mammal, (b) between 50 and 3000 mg purified L-glutamine, (c) between 50 and 10,000 mg purified vitamin C, (d) between 50 and 500 mg purified vitamin E, (e) between 10 and 100 mg purified Beta-carotene, and (f) between 1.0 and 25 mg purified vitamin $B_6$.

20. The composition of claim 19, further comprising one or more of the following purified components:

between 50 and 5000 mg L-arginine, between 5 and 50 µg chromium, between 50 and 150 µg folic acid, between 1 and 5 mg iron, between 10 and 50 mg magnesium, between 5 and 50 mg pantothenic acid, between 1 and 2.5 mg riboflavin, between 5 and 50 mg thiamine, between 0.5 and 10 mg vitamin A, between 10 and 1000 µg selenium, between 0.5 and 5 µg vitamin $B_{12}$, and between 1 and 50 mg zinc.

21. The composition of claim 20, wherein said composition comprises each said component.

22. The composition of claim 19 or 21, wherein said compound is gamma-L-glutamyl-L-cysteinylglycine or an ester or salt thereof.

23. The composition of claim 19 or 21, wherein said compound is gamma-L-glutamyl-L-cysteine or an ester or salt thereof.

24. The composition of claim 19 or 21, wherein said compound is N-acetyl-L-cysteine or an ester or salt thereof.

* * * * *